US008227255B2

(12) United States Patent
Fukumoto

(10) Patent No.: US 8,227,255 B2
(45) Date of Patent: Jul. 24, 2012

(54) BIOSENSOR AND METHOD OF ASSAYING OBJECT

(75) Inventor: Hirofumi Fukumoto, Fuji (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 736 days.

(21) Appl. No.: 12/359,866

(22) Filed: Jan. 26, 2009

(65) Prior Publication Data

US 2009/0191649 A1  Jul. 30, 2009

Related U.S. Application Data

(62) Division of application No. 10/569,802, filed as application No. PCT/JP2004/012383 on Aug. 27, 2004, now abandoned.

(30) Foreign Application Priority Data

Aug. 29, 2003 (JP) .................................. 2003-306508

(51) Int. Cl.
*G01N 25/18* (2006.01)

(52) U.S. Cl. ...................... 436/149; 435/173.1; 436/151; 436/806; 427/469

(58) Field of Classification Search .................. None
See application file for complete search history.

(56) References Cited

U.S. PATENT DOCUMENTS

| | | | |
|---|---|---|---|
| 5,981,297 A | 11/1999 | Basselt | |
| 6,057,167 A | 5/2000 | Shieh et al. | |
| 6,878,517 B1 | 4/2005 | Benson | |
| 7,172,904 B2 | 2/2007 | Engel et al. | |
| 2004/0023365 A1* | 2/2004 | Engel et al. | 435/287.2 |
| 2004/0033627 A1 | 2/2004 | Aytur et al. | |
| 2004/0137486 A1 | 7/2004 | Benson | |
| 2005/0106758 A1* | 5/2005 | Fukumoto et al. | 436/526 |

FOREIGN PATENT DOCUMENTS

| | | |
|---|---|---|
| JP | 2003-207511 | 7/2003 |
| JP | 2003-517843 | 6/3003 |
| WO | WO 97/45740 | 12/1997 |
| WO | WO 03/067258 | 8/2003 |

OTHER PUBLICATIONS

International Preliminary Report on Patentability (International Application No. PCT/JP2004/01283).
Japanese Office Action for Patent Application No. 2005-513, 478 dated Nov. 11, 2008.

* cited by examiner

*Primary Examiner* — Nelson Yang
(74) *Attorney, Agent, or Firm* — Finnegan, Henderson, Farabow, Garrett & Dunner, L.L.P.

(57) ABSTRACT

A biosensor capable of analyzing an object, such as antigen, antibody, DNA or RNA, through detection of magnetic field to thereby allow washout of unbound label molecules to be unnecessary, which biosensor is compact and available at low price, excelling in detection precision. Coils are arranged at an upper part and a lower part of a magnetic sensor using a hall element as a magnetic field detection element. An object and magnetic particles having an antibody capable of specific bonding with the object bound to the surface thereof are introduced in the magnetic sensor having a molecular receptor capable of specific bonding with the object attached to the surface thereof. Therefore, a change in magnetic field by magnetic particles bonded through the molecular receptor to the surface of the magnetic sensor is detected by means of the hall element. At that time, one applied magnetic field is set so that the magnetization intensity of magnetic particles falls within the range from initial magnetic permeability to maximum magnetic permeability while another applied magnetic field is set so that the magnetization intensity of some or all of the magnetic particles becomes saturated, and output signals are compared with each other. Thus, the amount of bonded magnetic particles can be identified.

7 Claims, 12 Drawing Sheets

*FIG. 7*
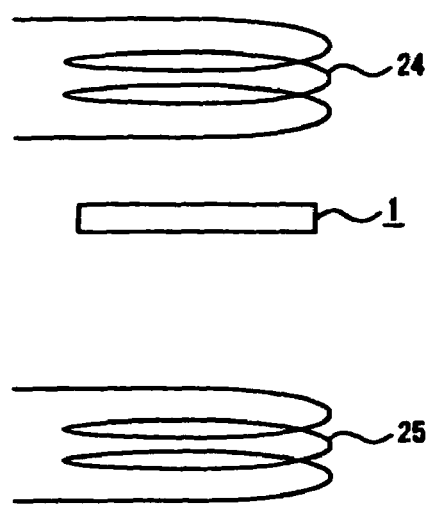
*FIG. 8A*  *FIG. 8B*
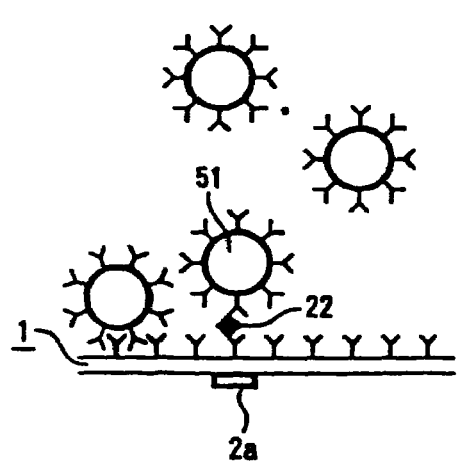 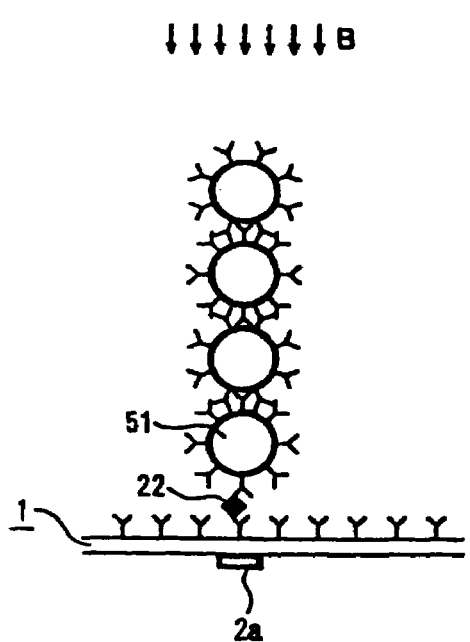

| ANTIGEN CONCENTRATION (ng/ml) | 0 | 0.1 | 1 | 10 | 100 |
|---|---|---|---|---|---|
| AVERAGE DEVIATION IN THE WEAK MAGNETIC FIELD (%) | 0.19 | 0.22 | 0.27 | 0.32 | 0.50 |
| AVERAGE DEVIATION IN THE STRONG MAGNETIC FIELD (%) | 0.18 | 0.20 | 0.22 | 0.23 | 0.31 |
| DIFFERENTIAL OF AVERAGE DEVIATIONS (%) | 0.01 | 0.02 | 0.05 | 0.09 | 0.19 |

BIOSENSOR AND METHOD OF ASSAYING OBJECT

This is a divisional application of U.S. application Ser. No. 10/569,802, filed Feb. 27, 2006 now abandoned, which is a National Stage of PCT/JP04/12383 filed Aug. 27, 2004, and claims the benefit of JP 2003-306508 filed Aug. 29, 2003, all of which are incorporated herein by reference.

TECHNICAL FIELD

The present invention relates to a sensor for measuring an amount of magnetic particles and a method of measuring the same, and in particular to a biosensor using magnetic particles and a method of assaying an object.

BACKGROUND ART

Recently, in clinical diagnosis/detection and analysis of the genes, immunological methods utilizing a specific interaction between specific molecules, such as an antigen and antibody thereto, and the like, are used to detect antigen, antibody, DNA (Deoxyribonucleic Acid), RNA (Ribonucleic Acid) and the like.

One of these methods, a solid phase binding assay includes a method using magnetic particles. FIG. 15 shows a schematic diagram of a solid phase assay using conventional magnetic particles.

As shown in the figure, the assay for an object 94 is carried out using a solid phase 91, a molecular receptor 95, a magnetic particle 92 and a secondary molecular receptor 93.

The solid phase 91 has a surface of the solid phase in contact with the sample solution and the molecular receptors 95 are immobilized thereto. Polystyrene beads, walls of a reaction vessel, substrates and the like are used as the solid phase 91.

The molecular receptor 95 is a substance that specifically binds to the object 94, such as antigen, antibody, DNA, RNA or the like, which exists in the sample solution. The molecular receptor 95 is such a molecule as antigen, antibody, DNA, RNA or the like, which can specifically bind to the object 94.

The magnetic particle 92 is a particle having magnetization and used as a labeling material. That is, by detecting the magnetic field formed by the magnetic particle 92, the amount of the magnetic particle 92 is determined, and the presence or absence, or concentration of an object 94 in a sample solution is determined. In addition to the magnetic particles 92, a substance that emit detectable signals, such as radioactive, luminescent and chemiluminescent materials, enzymes and the like, may be used as a label. The known assays using these labels include enzyme immunoassay (EIA) using antigen-antibody reaction, and chemiluminescent assays, such as a strictly defined chemiluminescent assay (CLIA) using an immunoassayed compound labeled with a chemiluminescent material, chemiluminescent enzyme immunoassay (CLEIA) in which enzyme activity is detected at a high sensitivity by using a chemiluminescent compound in the detection system, and the like.

The secondary molecular receptor 93 that is previously immobilized to the magnetic surface is an antibody that binds specifically to the object 94.

In the analysis shown in FIG. 15, firstly a test solution containing the object 94 is added to the solid phase 91 to which the molecular receptor 95 is immobilized beforehand. By this procedure the object 94 binds specifically. Other substances in the sample solution stay in the solution without binding to the solid phase 91. Next, the magnetic particles 92, on which the secondary molecular receptors 93 are immobilized, are added into the sample solution. By this procedure, the secondary molecular receptor 93 binds specifically to the object 94 that is bound specifically to the molecular receptor 95 immobilized onto the solid phase 91. Then, the magnetic particles 92 bound onto the solid phase is quantitated by detecting the magnetization of the magnetic particles 92. By this procedure, the concentration or the location of the object 94 bound onto the solid phase may be determined. The methods for detecting the magnetization using magnetoresistance elements disposed in array form are disclosed in the patent documents 1 and 2.

Further, the assays using these labels include sandwich assay in which the object bound specifically to the molecular receptor described above is bound specifically to another molecule label, and also competitive assay, in which the object and a different molecule label competes to bind to the molecular receptor.

Thus, in the conventional methods, signals from the label, such as light emission and the like, are detected by a device, such as an optical detection device and the like capable of detecting these signals. In these methods, it is necessary to capture signals only from the label of the molecule bound specifically to another molecule immobilized onto the solid phase. However, in the optical detection method, accurate analyses may not be carried out in the presence of unbound labeled molecules because the signals from these labels are also captured. Therefore, it is necessary to washout the unbound labeled molecules completely. Further, in the optical detection device, very weak optical signals need to be detected, which creates difficulty in making the device compact and low cost.

On the other hand, as disclosed in the patent document 1, it is not necessary to washout unbound labeled molecules in the method of detecting by the magnetoresistance element using the magnetic particles as the label. However, in a detection chip on which the magnetoresistance elements are disposed in array form, a switching circuit is needed to output the signals from each element independently. Electric interconnects are required from each element disposed in array form to the switching circuit. Therefore, this creates problems, such as difficulty in making compact and the like, because as the number of the elements are increased, the interconnects are more complicated and the more area is needed to accommodate the interconnects.

Similarly, in the detection device that detects magnetic flux in the patent document 2 described above, the detection circuit for the magnetic particles includes a bridge circuit composed of the magnetoresistance elements and transistors serving as switching elements. However, since the magnetoresistance element requires magnetic material, the steps for formation and processing of the thin magnetic film have to be carried out after a part of the circuit including the transistors is processed by a general production process for integrated circuits.

Further, the patent document 3 discloses the method for detecting magnetic particles, as in the patent document 1, by disposing the hall elements in an array-like formation.

However, in the patent document 3, the output signals of the hall elements to which the magnetic particles are not bound must be used as a standard for the output signals of the hall elements to which the magnetic particles are bound. Furthermore, since the output signal from the hall element to which the magnetic particles are bound is so small that the detection becomes difficult when the size of the magnetic particles is smaller than the size of the hall element.

The objective of the present invention is to provide a magnetic sensor, which is compact, inexpensive and with a higher detection sensitivity, and a method of measuring the amount of the magnetic particles. Further, applying this sensor and the method of measuring, the present invention provides a biosensor, which is compact, inexpensive and with higher detection sensitivity, and an assay method to analyze the objects, such as antigen, antibody, DNA, RNA and the like, by detecting the magnetism using the magnetic particles as a label, without the washout of the unbound labeling molecules.

Patent Document 1: U.S. Pat. No. 5,981,297, Description.
Patent Document 2: International Publication W097/45740, Pamphlet.
Patent Document 3: International Publication W003/67258, Pamphlet.

DISCLOSURE OF THE INVENTION

According to the present invention, there is provided the sensor including a magnetic sensor composed of a plurality of magnetic field detection elements arranged two dimensionally in X rows and Y columns (X and Y are natural numbers), which generate the output values according to the intensity of the detected magnetic field, and measuring an amount of magnetic particles present on the aforementioned magnetic sensor based on the output values, characterized in that the sensor comprises a signal processing means that determines the amount of the magnetic particles based on the dispersion of the output value distribution, which is obtained from the output value of a plurality of the magnetic field detection elements.

When an external magnetic field is applied to the magnetic sensor in a state where the magnetic particles are not bound to the magnetic sensor, there is no variation of output values of a plurality of magnetic field detector elements (in the case of the ideal condition that there is no variation of sensitivity of each magnetic field detection element). However, when the magnetic particles are bound to this magnetic sensor, the magnetic particles bound to the magnetic sensor cause local disturbance of the magnetic field applied to the magnetic sensor, which results in variation of output values of a plurality of magnetic field detector elements. Since the degree of this variation is dependent on the amount of bound magnetic particles, the bound magnetic particles can be quantified based thereon.

For evaluation of this degree of variation, it is preferable to use dispersion indices such as standard deviation, average deviation, variance and the like.

Further, the output value of the magnetic field detection element includes the output value, or values corresponding to intensity of magnetic field, wherein the values are obtained in the output values.

In further embodiment, the biosensor of the present invention is the aforementioned sensor and the magnetic particles bind to an object which binds to the magnetic sensor, and the biosensor of the present invention is characterized in that the signal processing means determines an amount of magnetic particles bound to the aforementioned magnetic sensor through the object and determines an amount of the object based on the amount of the magnetic particles.

In further embodiments, the biosensor of the present invention is characterized in that the magnetic particles bind specifically with the object that binds to the aforementioned magnetic sensor, and that the amount of these magnetic particles bound to the aforementioned magnetic sensor through the aforementioned object is determined.

In further embodiments, the biosensor of the present invention is characterized in that the aforementioned signal processing means determines the amount of the aforementioned bound magnetic particles based on the differential between the dispersion of the aforementioned output value distribution and the dispersion of the reference distribution obtained from the output value of a plurality of the aforementioned magnetic field detection elements in the state where the magnetic particles are not bound to the aforementioned magnetic sensor.

In such a way, when the sensitivity of each magnetic field detection element is nonuniform, an accurate measurement may be made by comparing the dispersion of the reference distribution with the dispersion of the output values distribution, after obtaining the reference distribution in the state where the magnetic particles are not bound to the magnetic sensor.

In further embodiments, the biosensor of the present invention includes a means for applying external magnetic field of greatly different intensities to the aforementioned magnetic sensor bound to the magnetic particles, wherein one of the aforementioned external magnetic field of greatly different intensities is such a strong magnetic field that the magnetization of at least some of the bound magnetic particles becomes saturated, and another external magnetic field is such a weak magnetic field that the aforementioned bound magnetic particles each have a magnetic permeability falling within a range from an initial magnetic permeability to a maximum magnetic permeability, and is characterized in that the aforementioned signal processing means determines an amount of the aforementioned bound magnetic particles based on difference between the dispersion of the aforementioned output value distribution when the aforementioned strong magnetic field is applied and the dispersion of the aforementioned output value distribution when the aforementioned weak magnetic field is applied.

Here, the output values of the magnetic field detection element include the output value, or, based on the values obtained when the strong magnetic field and weak magnetic field are applied, values corresponding to intensity of magnetic field in each case.

In further specific embodiments, the present invention provides the biosensor that includes a magnetic sensor composed of a plurality of magnetic field detection elements disposed two dimensionally in X rows and Y columns (X and Y are natural numbers), which generate output values according to intensity of detected magnetic field, and that measures an amount of magnetic particles bound to the magnetic sensor based on the output values. In further embodiments, a biosensor of the present invention including: a means for applying external magnetic field of greatly different intensities to the magnetic-sensor bound to the magnetic particles; a signal processing means that determines the amount of the bound magnetic particles by comparing output values of each of the magnetic field detection element when the external magnetic field of greatly different intensities is applied, is characterized in that one of the external magnetic field of greatly different intensities is such a strong magnetic field that the magnetization of at least some of the bound magnetic particles becomes saturated, and another external magnetic field is such a weak magnetic field that the bound magnetic particles each have a magnetic permeability falling within a range from an initial magnetic permeability to a maximum magnetic permeability.

In further embodiments, a biosensor of the present invention is characterized in that the strong magnetic field changes intensity within such a range that the magnetization of at least some of the bound magnetic particles becomes saturated, and the weak magnetic field changes intensity within such a range that the permeability of the magnetic particles changes from initial magnetic permeability to maximum magnetic permeability, and that the signal processing means obtains from a plurality of magnetic field detection elements changes in output values according to changes in intensity of external magnetic field, when external magnetic fields of greatly different intensities including the strong magnetic field and the weak magnetic field are applied, and determines the amount of the bound magnetic particles based on differentials of the changes in these output values.

This is based on the discovery by the present inventors that when external magnetic field, in which the magnetic permeability of the magnetic particle is between initial and maximum state, is applied, the change rate of the magnetic flux density at the detection element against the external magnetic field intensity becomes greater because magnetization of the magnetic particles is increased in proportion to the intensity of the external magnetic field, but when the external magnetic field intensity is increased further, the change rate of the magnetic flux density is getting smaller because the magnetization of the magnetic particles become saturated.

Below, a description is given using FIG. 1A. As shown in FIG. 1A, when an external magnetic field with a magnetic flux density B is applied in the absence of magnetic particle 51, the magnetic flux density detected by hall elements 2, magnetic field detection elements, is the same as the external magnetic field, B. In the condition that the magnetic particle 51 are bound, the magnetic flux density detected by the hall elements 2 is changed because the magnetic particle 51 are magnetized by the external magnetic field. Here, the external magnetic field is applied vertically to the magnetosensitive layer of the hall element 2.

FIG. 1B shows a relationship between the change rate of magnetic flux density against the change in intensity of the external magnetic field and distance from the bound magnetic particles. FIG. 1B is a graph showing the change rate of magnetic flux density to the external magnetic field with the magnetic flux density B at the position of the dotted line a in FIG. 1A, and the vertical axis represents the change rate of the magnetic flux density and the horizontal axis represents the position corresponding to the arrangement of the hall elements in FIG. 1A. Further, the solid line L1 represents the change rate of the magnetic flux density when a weak external magnetic field is applied so that the magnetic permeability of the magnetic particle 51 falls between the initial magnetic permeability and the maximum permeability (weak magnetic field), and the dotted line L2 represents the change rate of the magnetic flux density when a strong magnetic field is applied so that the magnetization intensity of some or all of the magnetic particles becomes saturated (strong magnetic field).

Since the magnetization of the magnetic particle 51 is proportional to the external magnetic field between the initial magnetic permeability and the maximum magnetic permeability, the change rate of the magnetic flux density is great, but as the intensity of the external magnetic field is increased, the change rate of the magnetic flux density is getting smaller because the magnetization of the magnetic particle 51 becomes saturated.

Also, directly under the bound magnetic particle 51 (the location of hall element 2a), the magnetic flux density is increased due to the magnetization of the magnetic particle 51, but at the location a little away from the directly under the magnetic particle 51 (the location of hall element 2b), the magnetic flux density is decreased due to the magnetization of the magnetic particle 51.

Further, when a strong external magnetic field is applied, the change rate of the magnetic flux density at the locations of the hall elements 2a and 2b is decreased in absolute value, although the change rate may be plus or minus, compared with that occurring when a weak external magnetic field is applied. The change rate of the magnetic flux at the location away from the magnetic particle 51 (the location of hall element 2c) is not affected by the intensity of the external magnetic field.

Therefore, by comparing the change rates of the magnetic flux density under a weak external magnetic field, where the magnetic permeability of the magnetic particles falls between the initial magnetic permeability and the maximum permeability with that under a strong external magnetic field, where magnetization of a part or all of the magnetic particles is saturated, for example, by judging whether they are different or not based on the output of the magnetic field detection elements, it can be determined whether the magnetic particles are bound near the magnetic field detection element or not. In the present invention, an amount of change in the output values (output change rate) of the magnetic field detection elements against the change in intensity of the external magnetic field is used as a value corresponding to the change rate of the magnetic flux density against the change in intensity of the external magnetic field.

Further, the external magnetic field, either strong or weak magnetic field, may be a DC magnetic field or AC magnetic field. At this time, applying a DC magnetic field so that the magnetization of the magnetic particles is saturated, makes the change rate zero and more accurate measurement possible.

FIG. 2A shows the relationship of the output change rates of a hall element that is a magnetic field detection element in a weak magnetic field (AC magnetic field) and a strong magnetic field (AC magnetic field+DC magnetic field). The vertical axis represents the output change rate of the hall element under application of a weak magnetic field and the horizontal axis represents the output change rate of the hall element under application of a strong magnetic field. The component of the AC magnetic field in the weak and strong magnetic fields is the same.

When the magnetic particles are not present on the hall element, and there is no noise or variation of sensitivity, the output change rate of the hall element in the weak magnetic field and in the strong magnetic field is the same, and 1. However, the sensitivities of a plurality of hall elements fabricated on a same sensor chip by the conventional CMOS process are not equal and varied due to the process fluctuation. Thus, the plots of the output change rate of a plurality of hall elements distribute to the direction of arrow Y1 on the line with a slope of 1 in FIG. 2A. Even though there is such a variation of the sensitivity among the hall elements, the outputs of the same hall element in the weak magnetic field and in the strong magnetic field are equal, and therefore there is no need for considering the calibration of the sensitivity, as long as comparing these outputs.

Next, when a magnetic particle is bound directly on top of a hall element, as explained in FIGS. 1A and 1B, the magnetic flux is concentrated in the weak magnetic field by the magnetic particle and the output change rate of the hall element is increased. In the strong magnetic field, the magnetization of the magnetic particle is saturated, and thus the concentrative effect by the alternating current component is reduced and the output change rate of the hall element does not increase as much as in the weak magnetic field (if the magnetization is completely saturated, the output change rate is not increased). Therefore, the output change rate is distributed to the direction of arrow Y2 in FIG. 2A.

When the magnetic particle is bound, not directly on the top of the hall element but at the location a little away from the top, the magnetic flux is converged directly under the magnetic particle as explained in FIGS. 1A and 1B and reduced. In this case the output change rate is distributed to the direction of arrow 3 in FIG. 2A.

Further, since noise is present in the real manufactured hall elements, the output change rate is distributed to all the direction as shown by arrow 4 in FIG. 2A.

Next, an example of the measurements for the output change rate in each hall element in the weak magnetic field (AC magnetic field) and the strong magnetic field (AC magnetic field+DC magnetic field) are shown when no magnetic particle is bound to any of the hall elements (FIG. 2B) and when the magnetic particles are bound to the surface of the sensor chip (FIG. 2C). The composition of the AC magnetic field in the weak and strong magnetic fields is the same.

When the magnetic particle is not bound, it is confirmed that the output change rates are distributed around the line with a slope 1 as shown in FIG. 2B.

When the magnetic particle is bound, as shown clearly in FIG. 2C, it is confirmed that the values of the output change rate in the weak magnetic field are greater and the dispersion condition of the plots widens to the direction of the vertical axis.

By these procedures, it can be decided whether the output change rate of the magnetic field detection element takes a different value or not when external magnetic fields of greatly different intensities are applied. Through such decision the binding (or not binding) of the magnetic particle may be judged, and the amount of the magnetic particles bound to the magnetic sensor may be determined. Thus, even if there are variations in the sensitivity and the like of each magnetic field detection element, accurate measurements may still be carried out. Because of that, operations for calibration of the variation of the sensitivity and the like of each magnetic field detection element, and arrangement of the reference hall elements not bound to the magnetic particles are unnecessary.

In further specific embodiments, the biosensor according to the present invention is characterized in that output values are obtained from a plurality of the aforementioned magnetic field detection elements first applying the weak magnetic field by the means for applying external magnetic field, and then another set of output values are obtained from a plurality of the magnetic field detection elements applying the strong magnetic field by the means for applying external magnetic field.

By such a procedure, a part of the magnetic particles bound to the surface of the biosensor is released by the strong magnetic field, and the signals may be obtained in the condition more similar to that the magnetic particles are not bound, making it possible to measure with higher accuracy.

In further embodiments, it is characterized in that the aforementioned means for applying external magnetic field can apply a DC magnetic field, and still further can apply an AC magnetic field.

Here, the DC magnetic field is a magnetic field with a constant direction and intensity, and the AC magnetic field is a magnetic field with the direction and intensity that alter periodically, for example, that can be generated by flowing alternating current in a coil.

In further embodiments, it is characterized in that the aforementioned weak magnetic field is an AC magnetic field with such an intensity that a magnetic permeability of the bound magnetic particle falls within a range from initial magnetic permeability to maximum magnetic permeability, and the aforementioned strong magnetic field is the AC magnetic field added with a DC magnetic field and is an external magnetic field with such an intensity that the magnetization of at least some of the bound magnetic particles becomes saturated.

In further embodiments, it is characterized in that the aforementioned signal processing means includes: a noise prediction means that predicts noise components from frequency components other than those corresponding to the AC magnetic field included in output values from the magnetic field detection elements; and a noise removal means that removes noise components from frequency components corresponding to the AC magnetic field included in output values from the magnetic field detection elements based on the noise components predicted by the noise prediction means.

Next, it is characterized in that magnetic particles bound to the magnetic sensor are associated with other magnetic particles in a direction of the magnetic flux formed by the external magnetic field.

In this way, it becomes possible to measure with higher sensitivity because the concentrative effect of magnetic flux is enhanced by the magnetic particles bound to the magnetic sensor, and the signal of the magnetic field detection element is amplified, by binding the magnetic particles, which are bound to the magnetic sensor through object and at the same time magnetized by the external magnetic field, with another magnetic particles, which are not bound to the magnetic sensor through object but magnetized by the external magnetic field, with the interaction of their magnetic force.

In further embodiments, it is characterized in that the aforementioned magnetic field detection elements generate output values in proportion to a magnetic flux density of a flux formed in a detection space capable of magnetic field detection.

Using the magnetic field detection element which generate the output values in proportion to the magnetic flux density in the detection area in this way, it is possible to increase the accuracy of measurement of the magnetic flux density in external magnetic field of greatly different intensities as described above.

In further embodiment, the aforementioned magnetic field detection element is characterized by including a hall element.

As described above, the measurement accuracy becomes superior by using the hall element which generates output values in proportion to the magnetic flux density in the detection area.

Next, it is characterized by further including a selection means for selecting an arbitrary element among a plurality of said magnetic field detection elements and obtaining output values therefrom.

By this procedure, information about 2 dimensional location of the magnetic particles present on the surface of the magnetic sensor may be obtained.

In further embodiments, it is characterized by further including a signal amplification circuit that amplifies output values of the magnetic field detection element selected by the aforementioned selection means and in that the magnetic sensor, the selection means and this signal amplification circuit are formed on a chip.

By this system, the influence of induced electromotive force by alternating current magnetic field may be reduced. That is, the use of alternating current magnetic field as an external magnetic field generates induced electromotive force in interconnects for obtaining signals from the sensor, and this is added as a noise to the signals. By including the signal amplification circuit, the amplified signals are retrieved, and thus, even if the induced electromotive force by the external magnetic field is added, this influence may be reduced.

Further, the magnetic sensor may be made compact and also may be used by disposing according to the sample solution.

In further embodiments, it is characterized in that the aforementioned hall element includes: a pair of current terminals; a gate electrode that control a current flowing between the pair of current terminals; and a pair of output terminals that are arranged so that a current flows in almost vertical direction against the current flowing between the pair of current terminals.

In further embodiments, the aforementioned gate electrode is connected to a gate electrode interconnect, which is common for said hall elements arranged in a same row; the aforementioned pair of current terminals are connected to a pair of current terminal interconnects, which are common for said hall elements arranged in a same row; and the aforementioned pair of output terminals are connected to a pair of output terminals, which are common for said hall elements, and it is characterized in that the aforementioned selection means selects an arbitrary element from a plurality of hall elements and obtains output value thereof, by selecting one from Y numbers of gate electrode interconnects, a pair from X numbers of pairs of current terminal interconnects and a pair from X numbers of pairs of output terminal interconnects.

By making common interconnects for each row and each column, the selection of a hall element in an arbitrary location may be carried out easily, and at the same time the number of interconnect may be reduced. By such a composition, production of a magnetic sensor suitable to an object becomes easier and also it is possible to make the sensor compact.

In further embodiments, it is characterized in that in each detection area capable of magnetic field detection by the aforementioned magnetic field detection elements, an area of a vertical cross section of a magnetic flux formed on a surface of the magnetic sensor is almost the same as a maximum cross section area of said magnetic particle.

By this system, the number of magnetic particles bound to the magnetic sensor and detected by the magnetic field detection elements is limited to about 1, and thus it is possible to suppress the variation of measured values due to detecting a plurality of magnetic particles and to improve accuracy of the analysis. Further, since this system is to limit the number of magnetic particles bound to the magnetic sensor which may exist in the detection space, the detection space is, for example, elongated to the direction of the magnetic flux formation, and the magnetic field detection elements may be able to detect another magnetic particles which are linked in a row along the direction of the magnetic flux formation, attracted by the magnetic particles bound to the magnetic sensor. This is a favorable case because detection sensitivity for the magnetic particles bound to the magnetic sensor is enhanced by another magnetic particles.

In further embodiments, it is characterized in that each of the aforementioned magnetic field detection element is arranged with a space so that each element detects different magnetic particles.

By this system, it is possible to suppress the interferences such as the neighboring magnetic field detection elements detect the same magnetic particle and the like.

In further embodiments, it is characterized in that surface of the aforementioned magnetic sensor is treated so that molecular receptors capable of binding to said magnetic particles may be immobilized thereto.

In further embodiments, it is characterized in that surface of the aforementioned magnetic sensor is treated so that molecular receptors capable of binding to said magnetic particles may be immobilized selectively to a specific area.

By this procedure, it is possible to control an amount of bound magnetic particles in the detection space and the like.

In further embodiment, it is characterized in that recesses corresponding to the magnetic particles in size are formed on the surface of the aforementioned magnetic sensor in the detection space capable of magnetic field detection, and that the molecular receptors capable of binding to the magnetic particles are present only in these recesses.

By arranging the recesses on the surface of the magnetic sensor in the detection space, the molecular receptors may be bound only to a specific area of the surface of the magnetic sensor. By this structure, it is possible to control an amount of bound magnetic particles in the detection space and the like.

In further embodiments, it is characterized in that a first magnetic field generating means, which generates a magnetic field that keeps away the magnetic particles from the surface of the aforementioned magnetic sensor so that the magnetic particles are not bound to the surface thereof, is arranged in a position facing the surface.

By keeping the magnetic particles away from the surface of the magnetic sensor, interference by unbound magnetic particles on the result of detection may be prevented. Also, by keeping unbound magnetic particles away from the surface of the magnetic sensor, operations such as washing out floating magnetic particles at the time of measurement and the like become unnecessary.

In further embodiments, it is characterized in that a second magnetic field generating means, which generates magnetic field that keeps the magnetic particles closer to the surface of the magnetic sensor, is further provided.

By this system, the binding of the magnetic particle to the surface of the magnetic sensor is expedited, and the measuring time may be shortened.

In further embodiments, it is characterized in that a second magnetic field generating means, which generates magnetic field that keeps the magnetic particles closer to the surface of the magnetic sensor, and a magnetic field device control means that operates the aforementioned first magnetic field generating means and the second magnetic field generating means alternately to generate magnetic field, so that magnetic particles not bound to the surface of said magnetic sensor are stirred, are still further provided.

By this system, the magnetic particles are stirred, and thus binding of the magnetic particles to the surface of the magnetic sensor is expedited, and the measuring time may be shortened.

In further specific embodiments, in another biosensor of the present invention including: a magnetic sensor, in which a plurality of magnetic field detection elements are arranged, the elements each producing an output value corresponding to the intensity of the detected magnetic field; and a signal processing means that determines an amount of magnetic particles bound to said magnetic sensor based on respective output value obtained from said plurality of magnetic field detection elements, the biosensor is characterized in that the signal processing means judges dispersion condition of the magnetic particles based on the output values obtained from the plurality of magnetic field detection elements, after introducing the magnetic particles to the magnetic sensor and before removing the unbound magnetic particles from the magnetic sensor.

By measuring in the weak magnetic field before unbound magnetic particles are removed by magnetic field, the amount of magnetic particles present on the surface of the magnetic sensor may be measured regardless whether the magnetic particles are bound or unbound. By this procedure, it may be confirmed that the magnetic particles are dispersed on the surface of the magnetic sensor.

In a method of assaying an object using a biosensor of the present invention, in which the magnetic particles bind specifically to an object, that binds to the magnetic sensor, it is characterized in that said the method of assaying an object includes: a step for determining an amount of the magnetic particles bound to the magnetic sensor through the object using the biosensor; and a step for determining an amount of the aforementioned object based on the amount of the aforementioned magnetic particles.

In another method of assaying an object of the present invention using a biosensor of the present invention, in which said magnetic particles are replaceable with an object bound to said magnetic sensor reversibly, the method is characterized in that this method includes: a step for determining an amount of the magnetic particles bound to the magnetic sensor replacing the object using the biosensor; and a step for determining an amount of the object based on the amount of the magnetic particles.

BRIEF DESCRIPTION OF THE DRAWINGS

FIG. 5B illustrates a sectional view at the dash-dotted line a;

FIG. 7 illustrates a schematic diagram of the whole biosensor of the first embodiment;

FIG. 8A illustrates a diagram describing the state of the magnetic particles on the surface of the sensor chip;

FIG. 8B illustrates a diagram describing the state of the magnetic particles on the surface of the sensor chip when magnetic field is generated from the upper coil;

BEST MODE FOR CARRYING OUT THE INVENTION

The biosensor of the embodiment of the present invention will be described by referring to diagrams as follows.

However, the invention is not limited to biosensors; but applicable to magnetic sensors in general that measure an amount of magnetic particles.

<First Embodiment>
(System Configuration of Biosensor)

Figure 3:
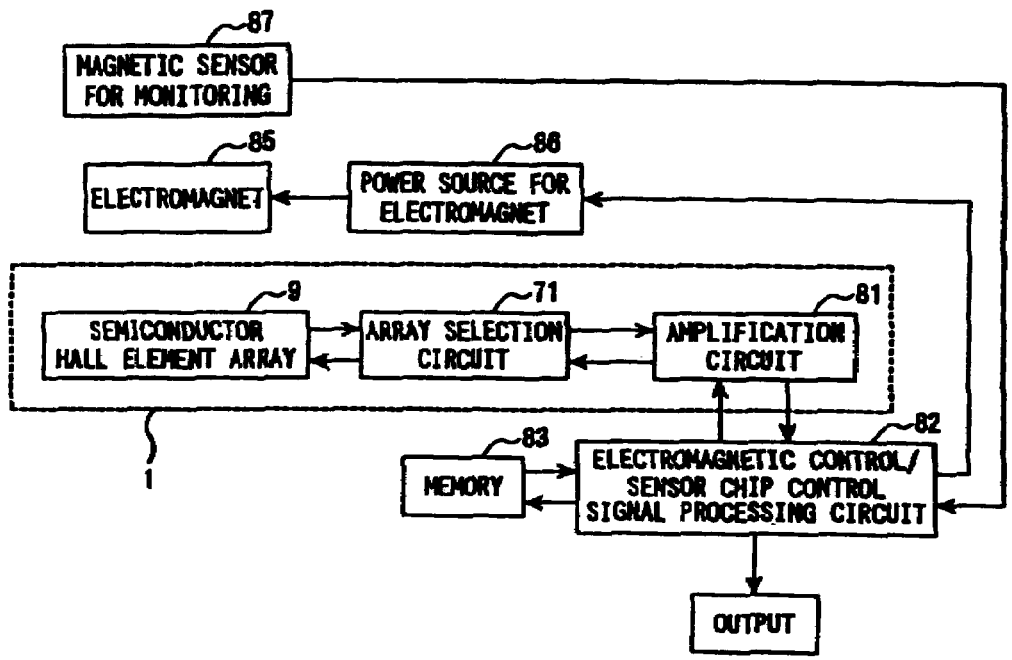
FIG. 3 illustrates a block diagram describing the biosensor circuit of the present embodiment.

FIG. 3 shows the system configuration of the biosensor of the present embodiment. The biosensor includes a sensor chip 1 to which a sample solution is introduced to carry out measurement and a measurement equipment which has a magnetic field generator which applies a magnetic field to the sensor chip 1, and circuitry to communicate with the sensor chip 1.

The sensor chip 1 is integrated with an array of hall elements 9, an array selection circuit 71, and an amplification circuit 81. The measurement equipment is installed with: a magnetic field generator including an electromagnet 85, a power supplier for the electromagnet 86 and a magnetic sensor for monitoring 87 which monitors the magnetic field by the electromagnet 85; a control circuit which controls sensor chip 1; a signal processing circuit (a signal processing means) which processes the output signals from the hall elements; and other control circuits 82 (for example, a control circuit (a control means for the magnetic field device) for the power supplier of the magnetic field generator). The sensor chip 1 is changed to a new one in each measurement.

(Configuration of the Sensor Chip)

Figure 4:
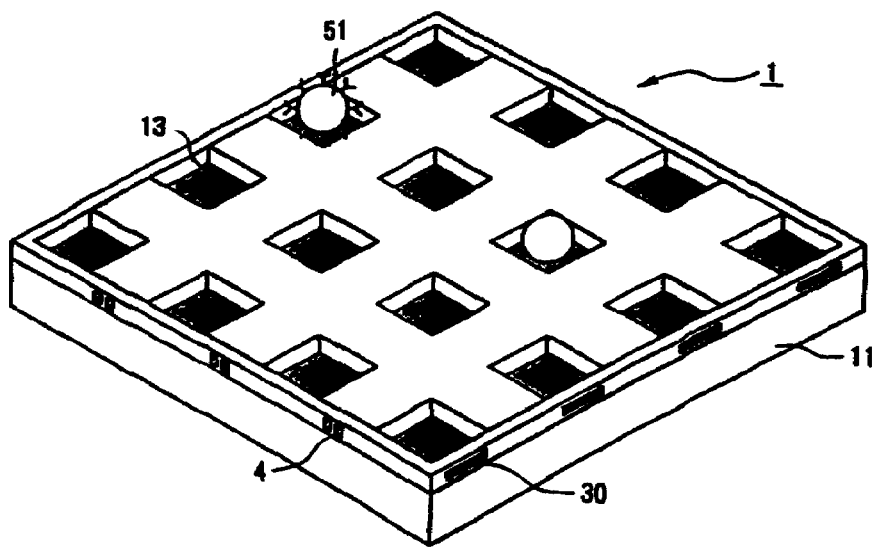
FIG. 4 illustrates a schematic diagram showing a part of the biosensor of the present embodiment.

FIG. 4 is a schematic diagram of a part of the sensor chip.

The sensor chip 1 is formed on a silicon substrate 11 by well-known CMOS (complementary metal-oxide semiconductor device) fabrication process. On the sensor chip 1, recesses 13 are formed spaced apart with a predetermined pitch. Under this recess 13, hall elements (magnetic field detection elements) are formed, and input and output of each hall element are carried out through a gate electrode 30 and a metal interconnect 4. The extreme surface is covered with silicon nitride film or silicon oxide film prepared by the plasma CVD (chemical vapor deposition) method.

After fabricating hall elements, an array selection circuit 71 and an amplification circuit 81 on the silicon substrate 11 by the CMOS fabrication process, molecular receptors (antigen, antibody, DNA, RNA and the like), which bind magnetic particles to the surface of the sensor chip 1, may be immobilized on the sensor chip 1 by treating the surface with silane coupling agent and the like.

The surface area of the hall element is supposed to be equal to the maximum cross section of the magnetic particle 51. In this way, the number of the magnetic particles 51 present in the magnetic field detectable by the hall element 2 may be kept about 1. Therefore, when the measurement is carried out by detecting the presence or absence of one magnetic particle 51 by the hall element 2, the detection of two or more of the magnetic particles 51 by the hall element may be prevented, and accurate measurements may be carried out. However, the measurement of the present invention is not limited to detecting the presence or absence of one magnetic particle 51 by the hall element. That is, the surface area of the hall element 2 may be equal to the maximum cross section of a plurality of the magnetic particles and a plurality of magnetic particles may be detected by the hall element.

Figure 1A:
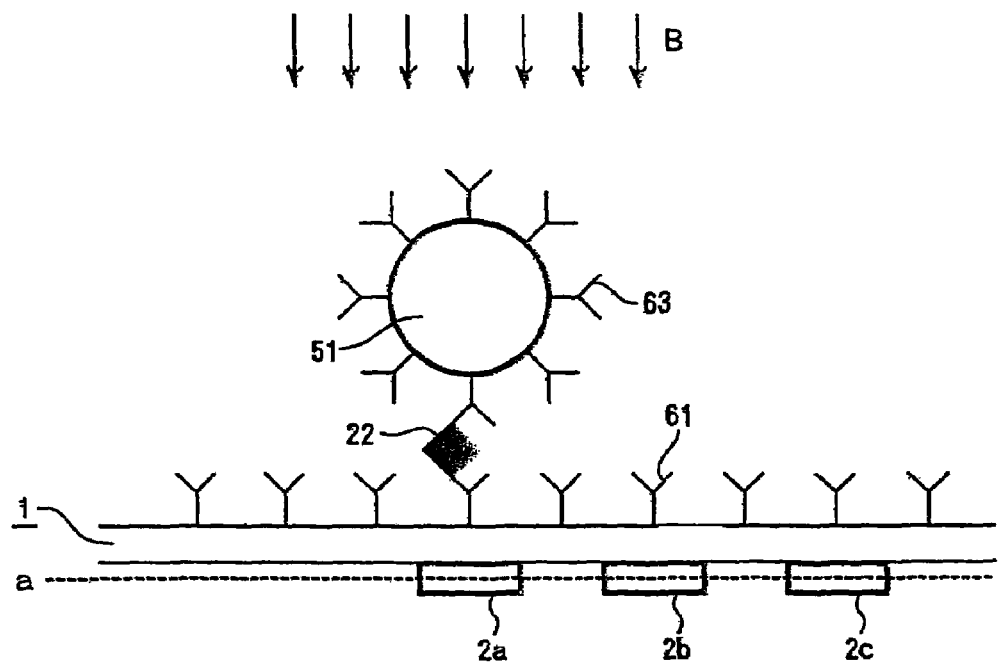
FIG. 1A illustrates a cross section of a hall element and its vicinity.
Figure 1B:
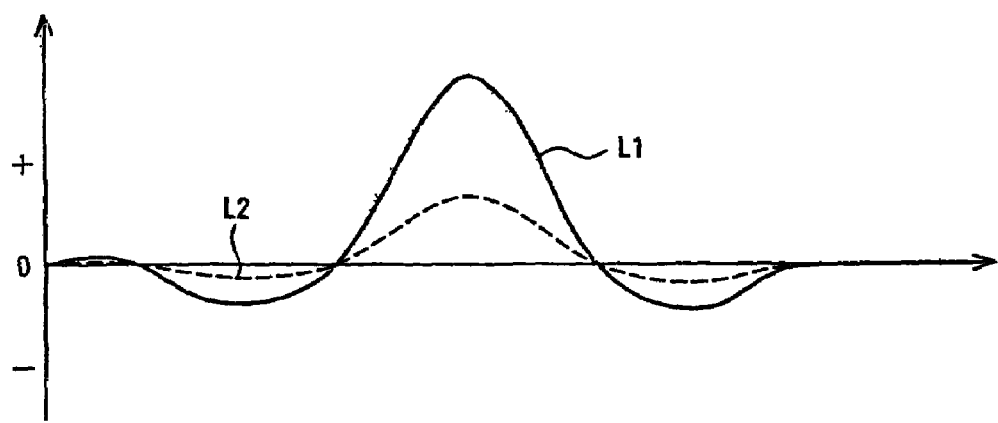
FIG. 1B illustrates the change rate of magnetic flux density.

Further, the arrangement of the hall elements, the space between the recesses 13 and the like are not limited in particular. As shown in the principle of detection of FIGS. 1A and 1B, the change rate of the magnetic flux density is changed not only at the hall element 2a where the magnetic particle is directly on the top, but also in the region near the magnetic particle such as at the hall element 2b where the magnetic flux density is reduced. Therefore, the molecular receptors 61 may be immobilized on the whole surface of the sensor chip 1 to detect the change in the magnetic flux density near the magnetic particle. Further, since the change rate in the area directly under the magnetic particle 51 where the magnetic flux density is increased is greater than in the surrounding area where the magnetic flux density is decreased as shown in FIG. 1B, the molecular receptors may be selectively immobilized directly on top of the hall elements so that the magnetic particles are bound only directly on top of the hall elements. Still further, hall elements may be arranged by separating with a distance of, for example, the hall element 2a and 2c as shown in FIG. 1A, so that the magnetic particle bound on top of the neighboring hall element has no influence.

(Structure of Hall Elements)

Next, the structure of hall elements will be described.

Figure 5A:
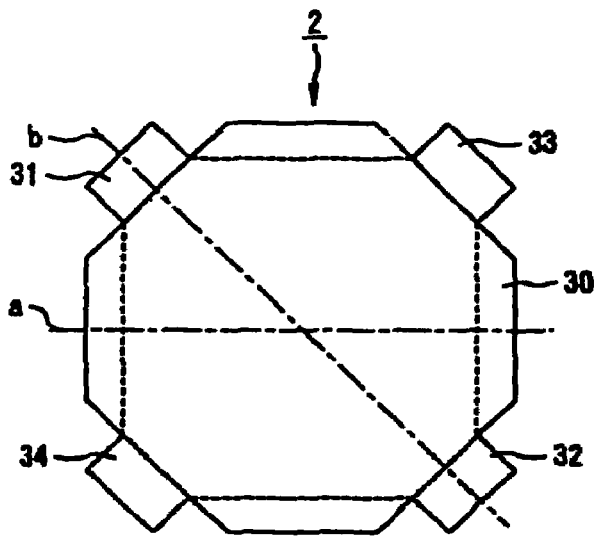
FIG. 5A illustrates a top view of the hall element 2.
Figure 5B:
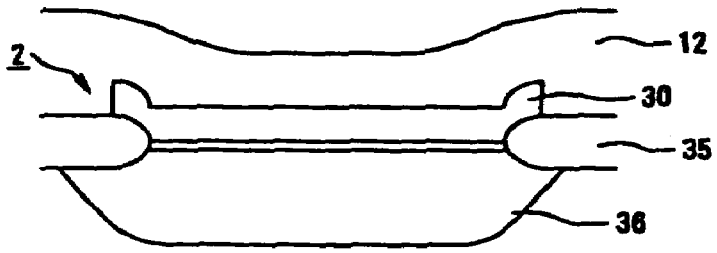
Figure 5C:
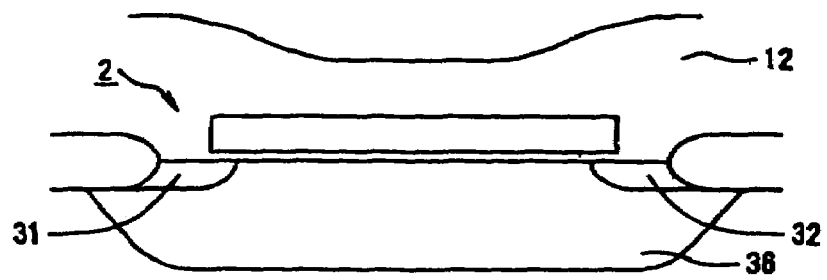
FIG. 5C illustrates a sectional view at the dash-dotted line b.

FIG. 5A is a top view of the hall element 2, FIG. 5B is a sectional view at the dash-dotted line a, and FIG. 5C is a sectional view at the dash-dotted line b. This hall element 2 is composed of a gate electrode 30, a source electrode 31, a drain electrode 32, an output electrode 33, 34 and an insulation layer 35, and formed in a P well region 36. The configuration is the same as the n type MOSFET except the output electrodes, and the metal interconnects to each electrode are omitted in the figures. The output electrodes 33, 34 are arranged so that the current flows vertically to the magnetic flux, which is formed almost vertically to the surface of the sensor chip, and the current flowing between the source drain electrodes.

The operation of this hall element 2 will be described. A bias is applied to the gate electrode 30, source electrode 31 and drain electrode 32 and the operation condition is similar to MOSFET. It is preferable that the operation condition at this time is in a linear region. If there is no external magnetic flux in this condition, the two output electrodes 33, 34 are in an equal potential. When an external magnetic flux is applied vertically to the surface of the hall element, a voltage proportional to the magnetic flux density is generated between the output electrodes 33 and 34 as a differential voltage.

(Array Arrangement of Hall Elements and Selection Method of Each Hall Element)

Next, the arrangement of the hall elements on the sensor chip and the method for selecting each hall element and obtaining outputs will be described.

Figure 6:
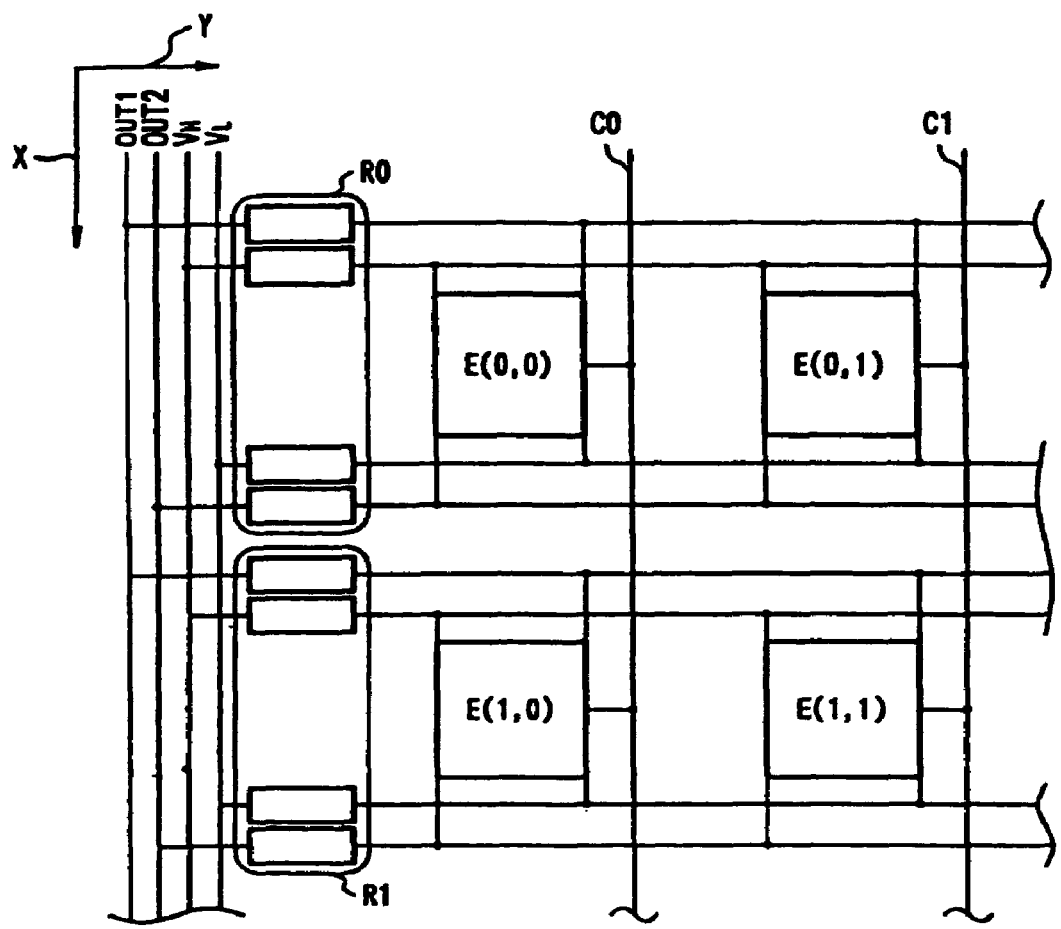
FIG. 6 illustrates a diagram describing the selection method for hall elements in array form in the present embodiment.

A source electrode, a drain electrode and a pair of output electrodes of each hall element (E (0, 0), E (0, 1), ... ) are connected to $V_L$, $V_H$, OUT1, OUT2 through switches (R0, R1, ... ) and the hall elements in the same row are connected in common. Also, the gate electrodes in the same column are connected to a common gate electrode interconnects C0, C1, ... In FIG. 6 columns and rows are shown in X and Y, respectively. $V_L$, $V_H$ are the interconnects to supply bias to the hall element, and OUT1, OUT2 are interconnects to output from the hall elements to the amplification circuit.

The case of selecting the hall element E(0, 0) will be described. Only the switch R0 is set on and switches R1, R2, ... are set off. Further, only the gate electrode interconnect C0 is set at a voltage that the hall element is in the active condition but the gate electrode interconnects C1, C2, ... are set at the voltage that the hall electrodes are not in the active condition, that is there is no current flowing between the source and drain even if a bias is applied to the source electrode and drain electrode.

At this time, $V_L$, $V_H$ are applied to the hall element E 0, 0), and the other elements in the same row and the source electrode and drain electrode, but current only flows through the hall element E (0, 0). The voltage corresponding to the magnetic flux density is generated at the output electrodes of the hall element E (0,0). Since the output electrode of other hall elements in the same row are not in the active condition, the output voltage of the hall element E (0,0) is outputted to OUT1 and OUT2 as it is. In this configuration, even if the number of arrays is increased, the number of interconnects in the array is the same and only switches are added at the edge. Therefore, the area of a sensor chip is almost proportional to the number of arrays, and a sensor chip with a large number of hall elements may be composed easily.

(Configuration of Electromagnet)

FIG. 7 shows the arrangement of an electromagnet. In the present embodiment, the electromagnet 85 includes an upper coil 24 that is arranged on the opposite location of the surface of the sensor chip 1 and a lower coil 25 that is arranged on the reverse side of the sensor chip 1.

The upper coil 24 is a means for applying external magnetic field and generates a magnetic field with a magnetic flux vertical to the sensor chip 1. This magnetic field is detected by the hall elements, and in the present embodiment, a weak magnetic field with a magnetic permeability of the bound magnetic particles falling within a range from initial magnetic permeability to maximum magnetic permeability and a strong magnetic field with magnetization that at least some of the magnetic particles becomes saturated are formed on the surface of the sensor chip. Further, in the present embodiment, this weak magnetic field is an AC magnetic field and the strong magnetic field is formed by adding a strong DC magnetic field to this AC magnetic field.

Still further, the upper coil 24 functions as a first magnetic field generating means which keeps magnetic particles away from the surface of the sensor chip 1 and is turned on when the magnetic particles are introduced to the sensor chip 1 and generates a magnetic field in which the magnetic flux density is increased in proportion to the distance from the surface of the sensor chip 1. By the operation of this upper coil 24, floating magnetic particles which are not bound to the surface of the sensor chip 1 are kept away from the surface of the sensor chip 1, and thus unbound magnetic particles do not affect the magnetic flux that is detected by the hall elements.

Furthermore, in place of the coil, for example; a permanent magnet may be used.

The lower coil 25 functions as a second magnetic field generating means which keeps magnetic particles closer to the surface of the sensor chip 1 and forms a magnetic field which is not for detecting magnetic particles. Then magnetic particles are introduced to the sensor chip 1, the lower coil 25 forms a magnetic field in which the magnetic flux density is increased with getting nearer to the surface of the sensor chip 1. By the operation of this lower coil 25, magnetic particles are attracted to the surface of the sensor chip 1, and the time from the introduction of the magnetic particles to their binding to the surface of the sensor chip 1 is shortened. It is effective for magnetic particles with diameter of 1 μm or less in particular because they have a tendency not to go down with gravity alone.

Also, in place of the coil, for example, a permanent magnet may be used.

Further, by operating the upper coil 24 and the lower coil 25 alternately by the magnetic device control means, the magnetic particles move up and down, and the binding between the object and magnetic particles may be promoted.

FIGS. 8A and 8B show the views of the surface of the sensor chip 1 when the magnetic field is formed by the upper coil 24 with the introduction of the magnetic particles. The floating unbound magnetic particles are attracted upward, but some of the floating magnetic particles near the surface of the sensor chip 1 and the one bound to the surface of the sensor chip 1 are magnetized by the magnetic field by the coil and are attracted each other. As shown in FIG. 8A, when the magnetic field is not applied, the magnetic particles 51 is not magnetized and some are bound to the surface of the sensor chip 1 through the object 22, some are present on the surface of the sensor chip 1 without binding and some are floating. When the external magnetic field is applied to this, the magnetic particles 51 are magnetized and attracted each other by this magnetization as shown in FIG. 8B. And to the magnetic particle 51 bound to the surface of sensor chip 1, other magnetic particles 51 are linked in a column along the direction of the magnetic flux of the external magnetic field. This condition makes the change in the magnetic flux at the hall element 2a greater than the condition of the presence of single magnetic particle 51 does. Also, the magnetization of the magnetic particles 51 has a tendency to be saturated more easily, making the measurement with a higher sensitivity possible.

(Operation of the Biosensor)

Figure 9:
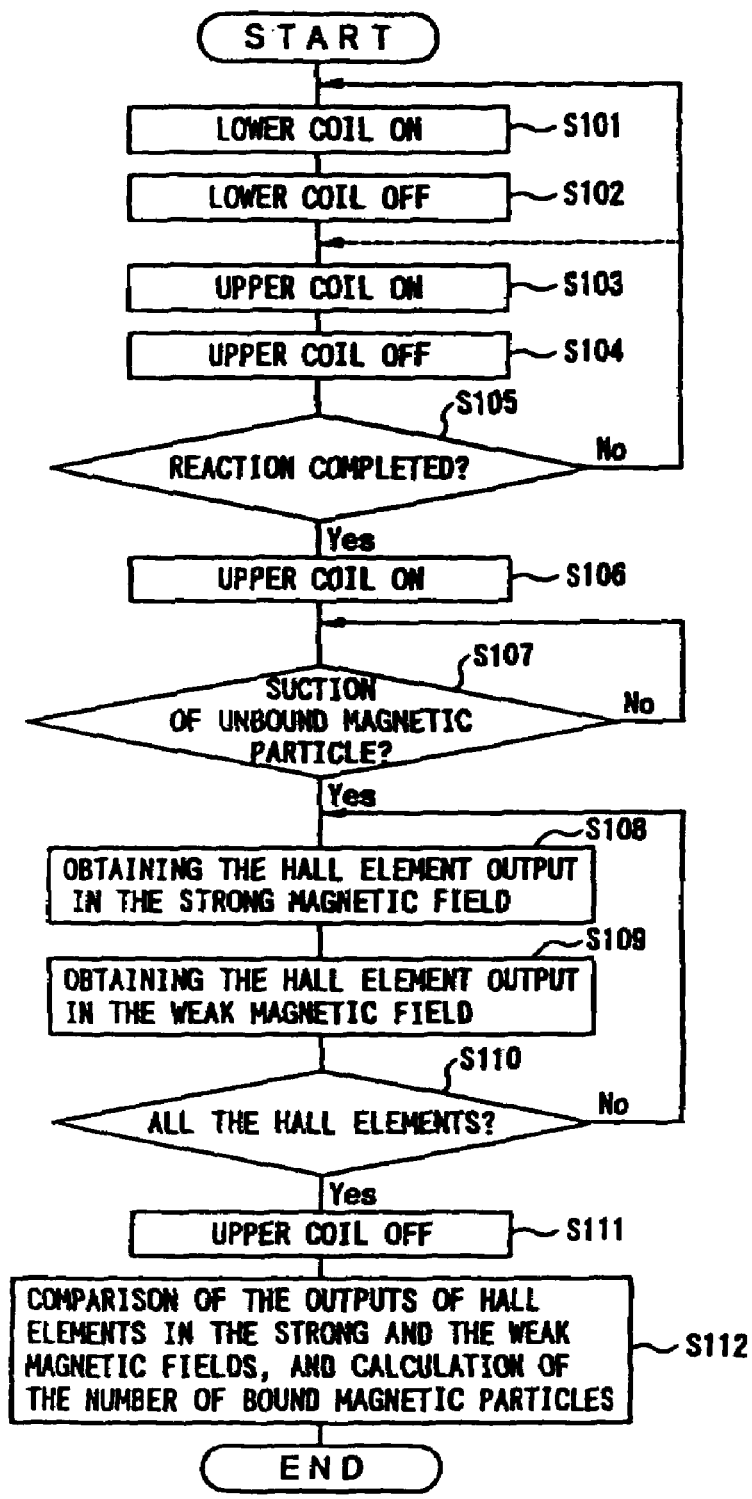
FIG. 9 illustrates a flow chart describing the circuit action of the entire biosensor of the first embodiment.

Next, the circuit operation of the biosensor of the present invention shown in a flow chart of FIG. 9 will be described.

At step S101, a magnetic field is generated by applying the current to the lower coil 25 with the magnetic particles placed over the sensor chip 1 and the magnetic particles 51 are attracted to the surface of the sensor chip. At this time the current applied to the lower coil 25 may be direct current or alternating current. Further, the current applied to the lower coil 25 is controlled so that the predetermined magnetic field is achieved, by measuring the magnetic field generated by the lower coil 25 using the magnetic sensor for monitoring 87.

At step S102, the magnetic field by the lower coil 25 is turned off.

At step S103, the current is applied to the upper coil 24 to generate a magnetic field to keep the magnetic particles 51 away from the surface of the sensor chip 1. At this time the current applied to the upper coil 24 may be direct current or alternating current. Further, the current applied to the upper coil 24 is controlled so that the predetermined magnetic field is achieved, by measuring the magnetic field generated by the upper coil 24 using the magnetic sensor for monitoring 87.

At step S104, the magnetic field by the upper coil 24 is turned off.

At step S105, the magnetic particles 51 is stirred in a sample solution, until the predetermined time or number is reached when the binding of the magnetic particles 51 to the surface of the sensor chip 1 is completed, by proceeding into step S101 again or step 105 and repeating steps of S101-S104.

At step S106, the current is applied to the upper coil 24 to generate a magnetic field to keep the magnetic particles 51 not bound to the surface of the sensor chip 1 away from the surface of the sensor chip 1, making possible to detect only the magnetic particles 51 bound to the sensor chip 1.

Step S107 is a waiting period until the predetermined time for completing the removal of the unbound magnetic particles 51 from the surface of the sensor chip 1.

After completing the removal of the unbound magnetic particles, in step S108, the strong magnetic field is generated from the upper coil 24 to obtain the output signals from the hall elements. Next, in step S109, the weak magnetic field is generated from the upper coil 24 to obtain the output signals from the hall elements. In particular, an address signal for selecting a specific hall element is sent from the sensor chip control circuit 82 in the measurement equipment to the array selection circuit 71 in the sensor chip 1. The array selection circuit 71 selects the designated hall element based on this address signal as described above. The output signal from the hall element is amplified by the amplification circuit 81 on the sensor chip. The amplified output signal is stored in the memory 83.

At step S110, it is decided whether the signals have been obtained or not from all the hall elements from which the output signal should be obtained, and if not, step S108 is repeated. By these procedures output signals from all the hall elements are obtained.

At step S111, the magnetic field by the upper coil 24 is turned off.

At step S112, the output values of each hall element at the strong and weak magnetic fields obtained at steps S108 and S109 are retrieved from the memory 83, and the number of bound magnetic particles is determined by comparing the output values of the hall elements in the signal processing circuit 82.

(Determination of Number of Magnetic Particles).

Next, described will be the comparison of the output values and determination of the number of magnetic particles by the signal processing circuit 82, after obtaining the output values of the hall elements as described above.

In an output value of an arbitrary hall element, the output change rates of this hall element to a small change in the AC magnetic field component of the upper coil 24 are calculated in the cases of the strong magnetic field and the weak magnetic field, and it is judged whether the respective output change rate is different or not. That is, when the magnetic particles 51 are not bound directly on the top or near a hall element as described above, the output change rates of this hall element in the strong and the weak magnetic fields are the same, but when the magnetic particles are bound directly on the top or near the hall element, the ratio of the output value of this hall element to the intensity of the magnetic field of the upper coil is different in the strong and the weak magnetic fields. Therefore, if the judgment is made that the output change rates are the same, then it is judged that the magnetic particles 51 are not bound directly on top or near the hall element, and if the output change rates are different, then it is judged that the magnetic particles 51 are bound directly on top or near the hall element. Further, in accordance with the size of the differential of the output change rate and the sign of the output change rate, it may be judged that the magnetic particles are not bound directly on top but near the hall element, and the like.

This judgment action is repeated in every hall element, and based on these judgment the number of bound magnetic particles is determined.

(Method for Measurement of Object Using the Biosensor)

By using the biosensor described above, and measuring the number of magnetic particles bound to the sensor chip, the concentration and the like of an object in a sample solution can be measured.

In the example of FIGS. 1A and 1B, antibodies are fixed on the surface of the sensor chip 1 as molecular receptors 61 that bind specifically to the object 22. Further, the magnetic particle 51 includes on the surface secondary molecular receptors 63 and this secondary molecular receptors 63 binds specifically with the object 22. Thus, the magnetic particle 51 specifically binds to the object 22 that is bound to the surface of the sensor chip L through the molecular receptor 61. By this procedure, the amount of the object 22 can be determined based on the measurement of the amount of the magnetic particles bound to the sensor chip 1 through the object 22, the molecular receptor 61 and the like.

The method of measuring of the objects using the biosensor is not limited to this method, and for example, the molecule that bind to the surface of the sensor chip 1 competitively with the object may be the magnetic particles. In this case, the amount of the magnetic particles which bind replacing the object is determined using the biosensor, and the amount of the competitive object can be determined based on the amount of the magnetic particles.

<Second Embodiment>

Next, the second embodiment of the present invention will be described.

The biosensor of the second embodiment is composed almost the same way as the biosensor of the first embodiment, but there is a difference in the manner of comparison of the output values and determination of the number of the magnetic particles by the signal processing circuit 82 after obtaining the output values from the hall elements. These are described below.

In this embodiment, first the dispersion of the output value distribution in the weak magnetic field is calculated from the output values of all hall elements when the weak magnetic field is applied. Next, the dispersion of the output value distribution in the strong magnetic field is calculated from the output values of all hall elements when the strong magnetic field is applied. Then, the differential between the dispersions of the output value distribution in the weak magnetic field and in the strong magnetic field is obtained, and the amount of the magnetic particles bound to the sensor chip is determined based on this differential.

That is, the variation of the output values from a plurality of magnetic field detection element, which is caused by the magnetic particles bound to the magnetic sensor, is converted to the dispersion, and the amount of bound magnetic particles is determined based on the degree of this variation.

Also, as described above, the change rate of the magnetic flux density at the hall element to the magnetic field by the coil is positive directly under the magnetic particle 51 and negative at the location a little away from the directly under as shown in FIG. 1B. When the magnetic particles are not present near the hall element, the change rate of the magnetic flux density is 0. Regardless of the change rate being positive or negative, the amount of the change when the magnetic permeability of the magnetic particles 51 is between the initial permeability and the maximum permeability is greater than the change rate when a part or the whole magnetization of the magnetic particle 51 is saturated. Thus, the differentials of the dispersions of the output values of all the hall elements in the weak magnetic field and in the strong magnetic field are proportional to the amount of the magnetic particles bound to the sensor chip, wherein the magnetic particles 51 is between the initial permeability and the maximum permeability in the weak magnetic field, and the magnetization of a part or whole of the magnetic particles are saturated in the strong magnetic field.

Further, in the ideal condition where the sensitivity of all the hall elements is the same, the deviation of the output values of all the hall elements is 0 when the magnetic particles are not bound in the weak magnetic region. When the magnetic particles 51 are bound on top of some hall elements, the dispersion is dependent on the amount of the bound magnetic particles because the output values of the hall elements that are bound to the magnetic particles 51 are changed. Therefore, the amount of bound magnetic particles 51 can be obtained. However, in reality, the sensitivity of the hall elements on the sensor chip 1 may vary to some extent due to the production process and the deviation is not 0 when the magnetic particles 51 are not bound. However, each of the dispersion of the output value distribution in the strong magnetic field and in the weak magnetic field is equal, and the differential between the dispersions is 0. When magnetic particles are bound on top of some of the hall elements, the change rate may be plus or minus depending on the location of the binding but it is greater in bound condition than in the state where the magnetic particles 51 is not bound. Further, since the amount of change in the change rate is greater in the weak magnetic field than in the strong magnetic field, the dispersion is also greater in the weak magnetic field than in the strong magnetic field when the magnetic particles 51 are bound. Thus, in the condition where the magnetic particles 51 are bound, there is a differential of the dispersions of the output vales of all the hall elements in the weak magnetic field and in the strong magnetic field, wherein in the weak magnetic field, the magnetic permeability of the magnetic particle 51 falls between the initial permeability and in the strong magnetic field, the maximum permeability and the magnetization of some or all of the magnetic particles are saturated.

Figure 2A:
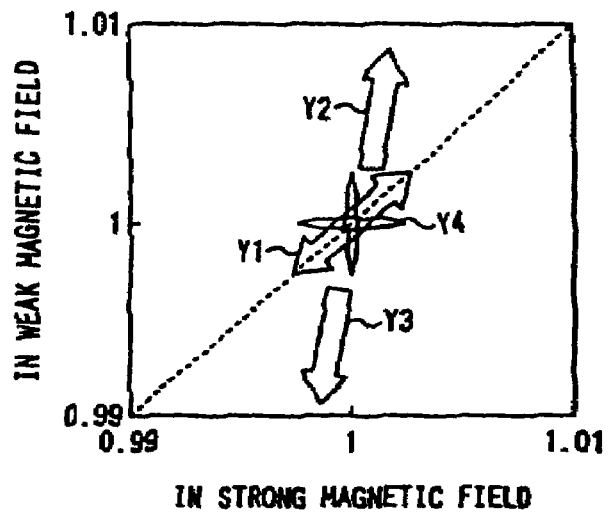
FIG. 2A illustrates the relationship of the output change rate of the hall elements in the weak and strong magnetic fields.
Figure 2B:
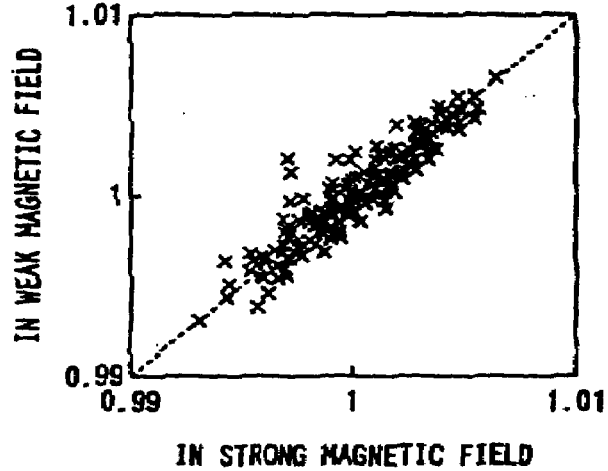
FIG. 2B illustrates the output change rate when any of the hall element is not bound to the magnetic particle.

In an example of real measurements, as shown in FIG. 2B, when the magnetic particles are not bound, the output change rates are distributed around a line with a slope of 1, confirming that the dispersions in the weak magnetic field and in the strong magnetic field are almost the same.

Figure 2C:
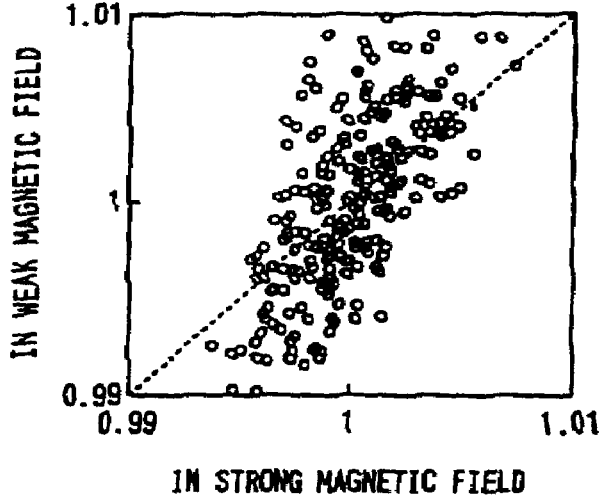
FIG. 2C illustrates the output change rate when the magnetic particle is bound to the surface of the sensor chip.

When the magnetic particles are in bound condition, the output change rate in the weak magnetic field is greater and the dispersion of the plots is spreading to the direction of the vertical axis as clearly seen in FIG. 2C. That is, the dispersion in the weak magnetic field becomes greater than that in the strong magnetic field and it is confirmed that the binding of the magnetic particles can be detected by obtaining the differential.

<Third Embodiment>

Next, the third embodiment of the present invention will be described. The biosensor of the third embodiment is composed in almost the same way as the biosensor in the first embodiment but the configuration of the signal processing circuit 82 is a little different. Following is the description.

In the present embodiment, the signal processing circuit 82 further includes: a noise component prediction part that predicts the noise component from the frequency component other than that corresponds to the AC magnetic field in the output value of hall elements; and a noise component removal part that removes, based on the predicted noise component, the noise component from the frequency component which corresponds to the AC magnetic field in the output value of hall elements.

The noise component prediction part is composed of an AD converter and a high speed Fourier converter, and carries out Fourier conversion of the output signal of the hall element and calculates the predicted noise level in the frequency component that corresponds to the AC magnetic field, based on the trend of the output level of the frequency spectra other than the frequency corresponding to the AC magnetic field.

Figure 10:
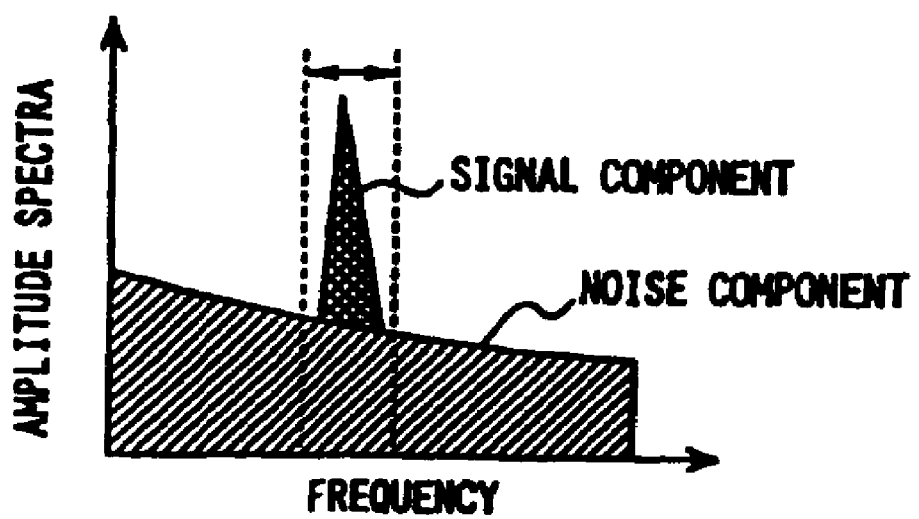
FIG. 10 illustrates a frequency spectrum of the output signal of the hall element by Fourier transform.

The frequency spectra obtained by Fourier transformation of the output signal of the hall element is shown in FIG. 10. The alternating current component of the magnetic flux on the sensor chip 1, by the external magnetic field applied to the sensor chip 1 and the magnetic particle 51, is composed of the frequency of the alternating current component of the external magnetic field and the frequency component corresponding to its harmonic waves. Since the output signals of the sensor contains noise, the Fourier conversion results in the spectra, as shown in the figure, covering the entire range of frequencies. As shown in the figure the signal component appears at the specific frequencies. The noise component includes mainly thermal noise that is not dependent on frequencies and the flicker noise that is proportional to the reciprocal of frequency. Since these noise components change against frequencies almost continuously, the noise level of the frequency, at which the signal appears, can be estimated from the spectra of the neighboring frequencies. Thus, the true signal component can be obtained by subtracting this noise level from the level of the sensor output.

The noise removal part calculates: a ratio of the true signal component, after removing the noise level based on the calculated noise level by the noise component prediction part, to the entire frequency component corresponding to the AC magnetic field; and obtains the true signal component by obtaining the output corresponding the ratio, when the frequency component corresponding to the AC magnetic field is extracted from the output signal of the hall element.

By doing this, the noise shown in FIG. 2A that varies in all the directions may be reduced, and the accuracy of the measurement becomes excellent.

<Fourth Embodiment>

Next, the fourth embodiment of the present invention will be described.

The biosensor of the fourth embodiment is composed similar to the biosensor of the first embodiment but the action in the measuring is different. Following is the description.

Figure 11:
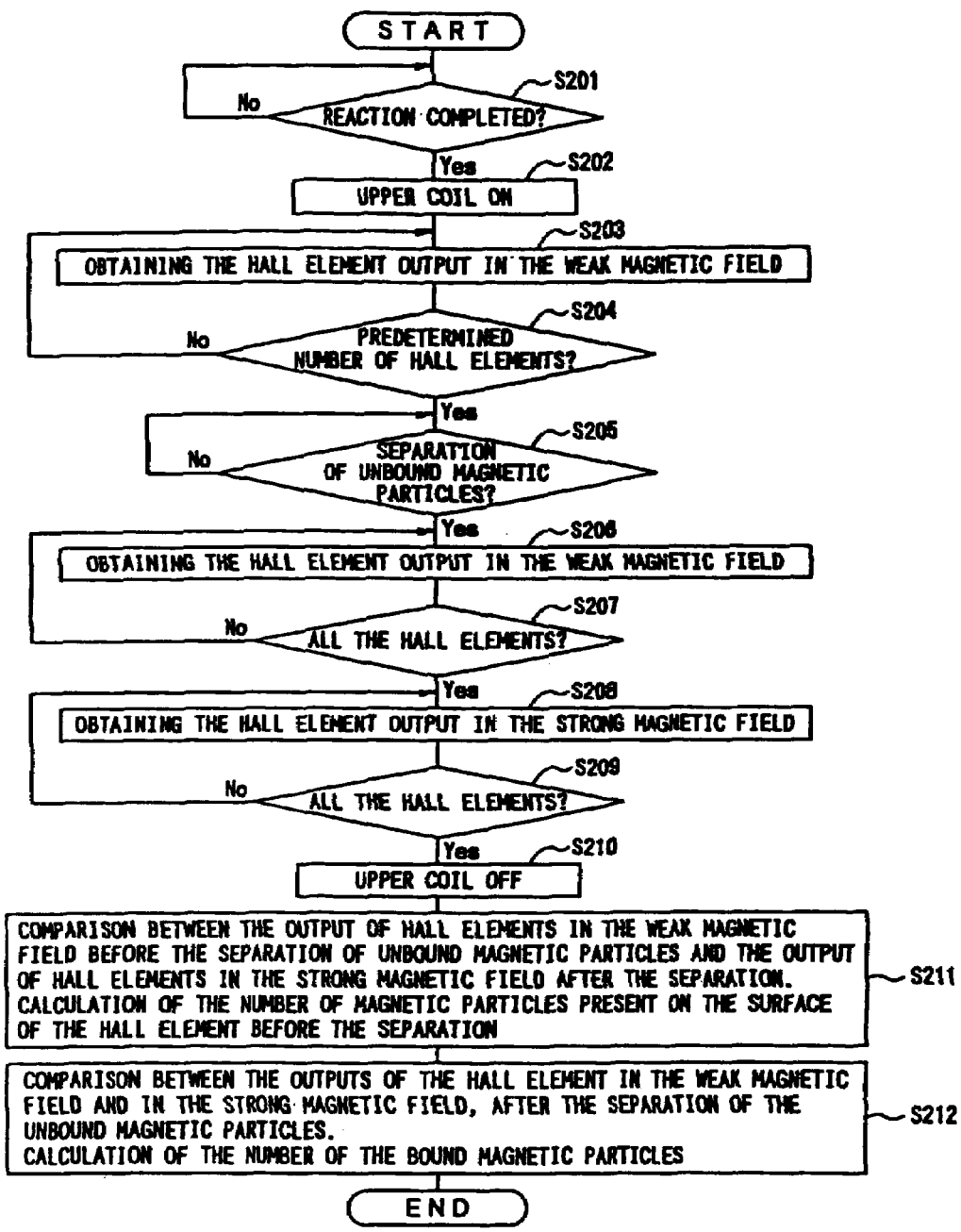
FIG. 11 illustrates a flow chart describing the circuit action of the entire biosensor of the second embodiment.

The action of the biosensor of the present embodiment is shown in a flow chart of FIG. 11. The description will not be made on the same point of the first embodiment.

At step S201, the magnetic particles 51 are introduced to the sensor chip 1 and stand until the predetermined binding of the magnetic particles 51 to the sensor chip 1 is completed. At this point, the binding of the magnetic particles 51 to the sensor chip 1 is promoted by stirring the sample solution by activating the upper coil 24 and lower coil 25 alternately as in the steps S101-S105 in the first embodiment.

At step S202, the weak magnetic field is generated by the upper coil 24, and at step S203, the output signal of a hall element is obtained and stored in the memory 83. These procedures are repeated until the output signals from the predetermined number of the hall elements are obtained (step S204).

At step S205, the predetermined magnetic field is generated by the upper coil 24, and stand for the predetermined time for removing of the unbound magnetic particles 51 from the surface of the sensor chip 1 is completed.

At step S206, the weak magnetic field is generated from the upper coil 24 and the output signal of a hall element is obtained and stored in the memory 83. At step S207, it is judged whether the signals are retrieved from all the hall elements, from which the signals should be retrieved, and in the case the signal not retrieved (No.) then S206 is repeated. By these procedures, the output signals of all the hall elements are obtained.

At step S208, the strong magnetic field is generated by the coil 24, the signal of a hall element is obtained and stored in the memory 83. At step S209, it is judged whether the signals are retrieved from all the hall elements, from which the signals should be retrieved, and in the case the signal not retrieved (No.) then S208 is repeated. By these procedures, the output signals of all the hall elements are obtained. When all the signals are obtained, the magnetic field of the upper coil 24 is shut off (step S210).

At step S211, the output value of each hall element obtained at step S203 and S208 is retrieved from the memory 83, and the output values of the hall elements are compared in the signal processing circuit 82. Then, the number of magnetic particles present on the sensor chip 1, regardless of whether bound or unbound, is determined before the unbound magnetic particles are removed from the sensor chip 1. By doing this, it can be confirmed whether the measurement is carried out under the state where the magnetic particles are evenly disperse.

At step S212, the output values of hall elements obtained at step S206 and S208 are retrieved from the memory 83 and compared in the signal processing circuit 82, and the number of bound magnetic particles is determined.

The method for determining the number of magnetic particles shown in the first and the second embodiment may be used as a method for determining the number of magnetic particles in the steps S211 and S212.

By carrying out the measuring in the strong magnetic field after the measuring in the weak magnetic field, some of the magnetic particles bound to the surface of the magnetic sensor are released and the signals may be obtained in the closer condition where the magnetic particles are not bound, and thus more accurate measurement can be made.

The invention described above will be described based on the examples.

EXAMPLE 1

The hall elements shaped as shown in FIGS. 5A to 5C that were arranged in array like arrangement and further, an array selection circuit and an amplification circuit were fabricated on a same silicon substrate. The distance between the source electrode 31 and the drain electrode 32 was about 6.4 μm and the distance between the sensitive face, that was a channel formed under the gate electrode 30 and the surface of the insulation layer 12 is about 2.8 μm. The pitch of the hall elements arranged array-like was 12.8 μm. The voltage applied between the source electrode of the hall element selected by the array selection circuit and the drain electrode was about 4V, and between the source electrode and the gate electrode was about 5V.

At the time of the measurement, an AC magnetic field with an effective intensity of 50 gauss in the weak magnetic field was applied, and in the case of the strong magnetic field, in addition to the AC magnetic field with an effective intensity of 50 gauss, the DC magnetic field with a intensity of 200 gauss was applied by a coil.

Figure 12:
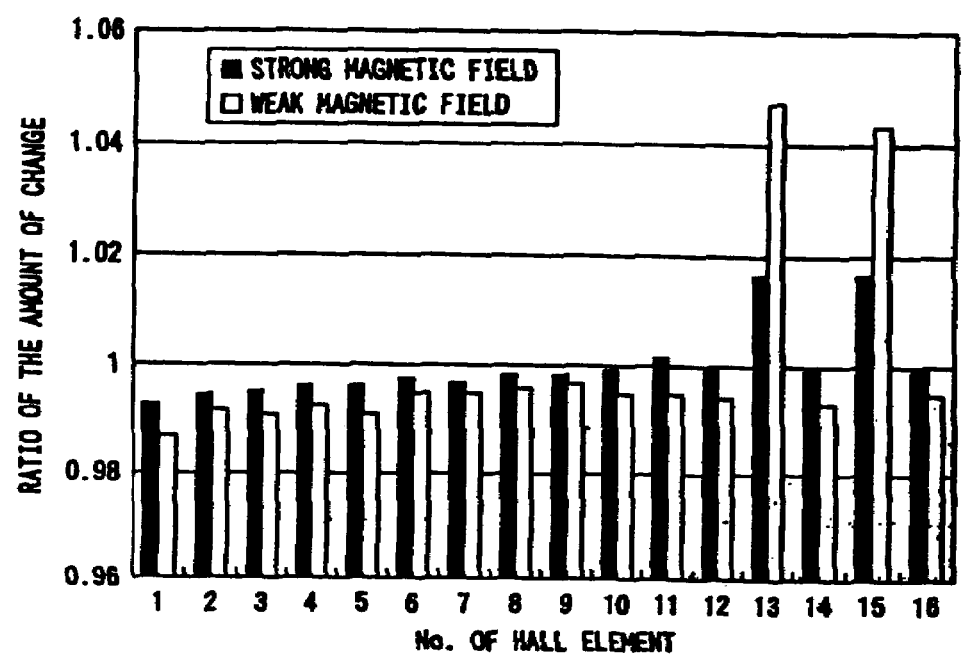
FIG. 12 illustrates a diagram describing the result of the measurement in the example 1.

On the sensor chip, magnetic particles with a diameter of 4.5 μm made by Dynal Inc. (Commercial Name: DYNA-BEADS) were bound. The result of the measurement is shown in FIG. 12. The ratio of the amount of the change of the alternating current component of the output of each hall element to the small change in the component of the AC magnetic field applied by the coil is shown. The measurements were carried out on the 128 hall elements on the sensor chip, and the figure shows the result of some hall elements. In the weak and strong magnetic fields, there was almost no difference in the outputs of the hall elements not bound to the magnetic particles against the magnetic field by the coil.

However, the outputs of the 13th and 15th hall elements that were bound to the magnetic particles were greater in the weak magnetic field than in the strong magnetic field.

If the magnetization of the magnetic particles was completely saturated in the strong magnetic field, the output of the sensor not bound to the magnetic particles should have been the same level, but, since the magnetization was not saturated, there was a difference even in the strong magnetic field. However, where the magnetic particles were not bound, there was no difference between the weak and strong magnetic field, and where the magnetic particles were bound, a clear difference was seen between the strong and weak magnetic field, and thus the magnetic particles bound to the surface can be detected (the method of determining the number of magnetic particles shown in the first embodiment).

Since the magnetic particles with a size similar to the hall elements were used in FIG. 12, the bound magnetic particles can be clearly detected. Further, the average deviations of all the 128 hall elements in the strong and weak magnetic fields are 0.56% and 1.48%, respectively, and from this differential the presence or absence of the magnetic particles can be judged (the method of determining the number of magnetic particles shown in the second embodiment).

EXAMPLE 2

Figure 13A:
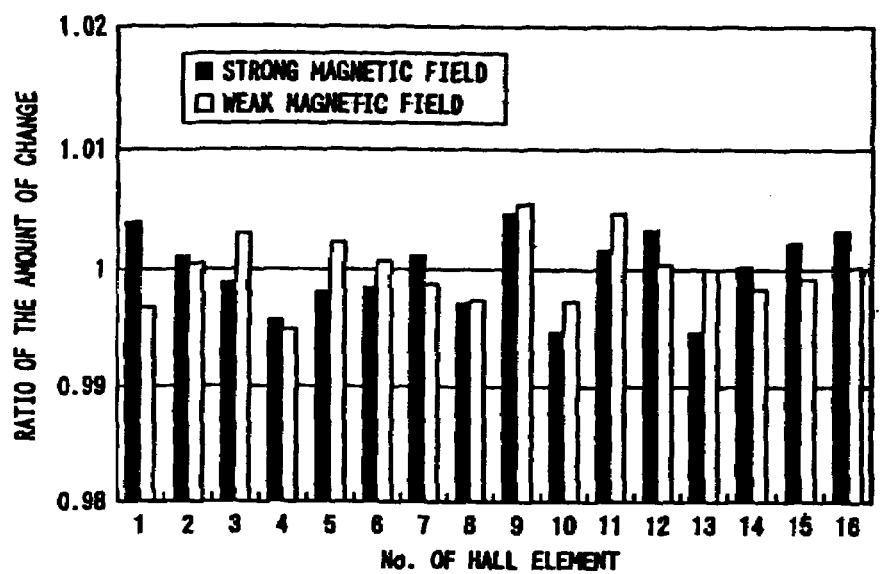
FIG. 13A illustrates a graph showing the result of the measurement in the example 2 where the magnetic particles are unbound.
Figure 13B:
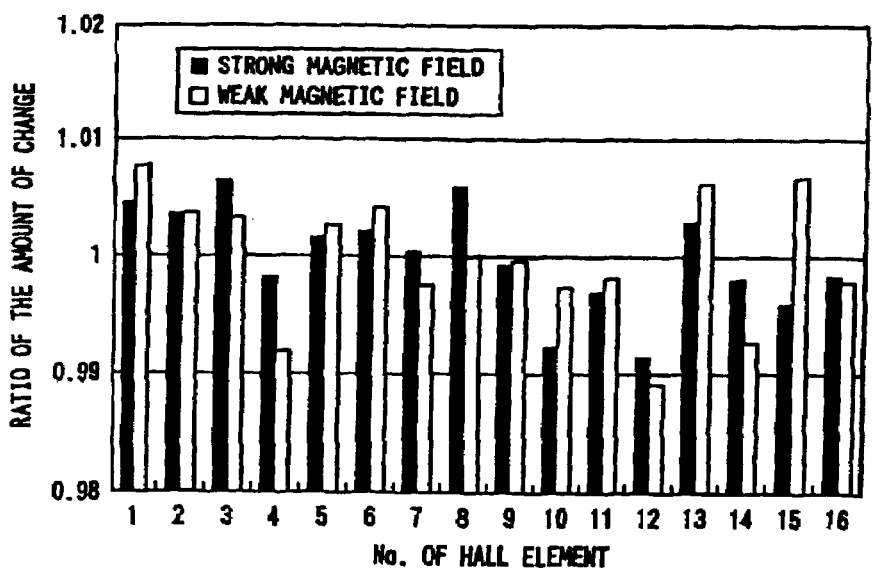
FIG. 13B illustrates a graph showing the result of the measurement in the example 2 where the magnetic particles are bound.

FIG. 13A shows the result of measurement when the magnetic particles were not bound to the sensor chip that was similar to the one in the example 1, and FIG. 13B shows the result of the measurement when the sensor chip was bound to the magnetic particles with a diameter of 1 μm made by Dynal Inc. The vertical axis represents the ratio of the amount of the change in the alternating current component of the output of each hall element to the micro-change in the AC magnetic field component applied by the coil. The measurements were carried out in each of all the 128 hall elements, and the figure shows the results of only some of the hall elements. In this case the magnetic particles were small compared to the size of the hall element, and thus a plurality of magnetic particles could bind to one hall element. However, since the volume was also small and the magnetization by the magnetic field applied by the coil was small, the change in the magnetic flux density on the hall element was small.

FIG. 13A shows that the output value of each hall element is varying although the magnetic particles are not bound. On the other hand in FIG. 13B where the magnetic particles are bound, it can not be judged whether the magnetic particles are bound or not, because the magnetization of the magnetic particles is small and the output value from each hall element is varied.

The differential of the average deviations of the output of all the 128 elements between the strong and weak magnetic fields were 0.02% without magnetic particles and 0.12% with bound magnetic particles. This result indicates that even if the judgment can not be made on the binding of the magnetic particles from the outputs of each hall element due to the magnetization of the magnetic particles being too small, the judgment still can be made on the binding of the magnetic particles by obtaining the differential of the average deviations of the outputs of a plurality of hall elements (the method of determining the number of magnetic particles shown in the second embodiment).

EXAMPLE 3

Figures 14, 15:
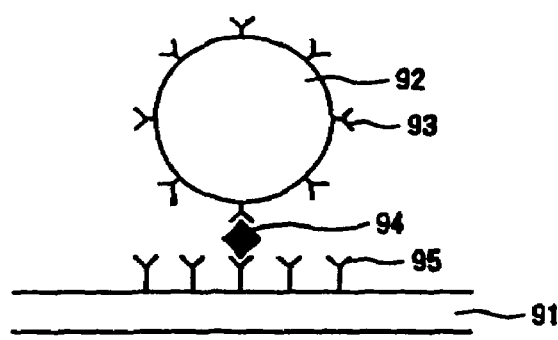
FIG. 14 is a table showing the test result of the example 3.
FIG. 15 illustrates a schematic diagram describing the solid phase analysis using conventional magnetic particles.

The magnetic particles with a diameter of 1 μm made by Dynal Inc. were bound to the sensor chip on which the 256 hall elements were arranged. At this time, an antigen derived from Haemophilus influenzae was used as an object. FIG. 14 shows the average deviation of the outputs of the hall elements against the antigen concentration in the weak and strong magnetic fields, and the differential of the average deviation. As seen in the figure, the differential of the average deviation increases with the increase of the antigen concentration.

This result indicates that even if the judgment cannot be made on the binding of the magnetic particles from the outputs of each hall element due to the magnetization of the magnetic particles being too small, the judgment still can be made on the binding of the magnetic particles by obtaining the differential of the average deviations of the outputs of a plurality of hall elements. Further, it was confirmed that even if the antigen concentration is 1 ng/ml or lower, the measurement of the antigen concentration was possible based on the number of bound magnetic particles.

Industrial Applicability

The biosensor of the present invention can be used for measuring the amount of magnetic particles, and further, for clinical diagnosis/detection, analysis of the genes and the like, by immunological means that detects antigen, antibody, DNA (Deoxyribonucleic Acid), RNA (Ribonucleic Acid) and the like, using the specific binding between certain molecules, such as the binding of an antigen labeled with magnetic particles to the antibody to this antigen and the like.

Since the biosensor of the present invention determines the amount of the magnetic particles bound to the magnetic sensor, based on the dispersion of the distribution of the output values of a plurality of the magnetic field detection elements, or based on the output value change in the magnetic field detection elements against the change in intensity of the external magnetic field, it is possible to make accurate measurements. Further, since the external magnetic fields of greatly different intensities are applied in the condition where the magnetic particles are bound, and the measurements are carried out based on the output values of the magnetic field elements in each magnetic field, even if the characteristics such as sensitivity and the like are varied, a reference value of the magnetic field may be obtained by each individual magnetic field detection element and also the reference value may be obtained in the condition where the magnetic particles and objects are introduced, it is possible to make measurements rapidly and accurately. Further, using hall elements as the magnetic field detection elements for this purpose, the accuracy of measurement becomes excellent. Still further, the biosensor becomes inexpensive and compact by using hall elements as the magnetic field detection elements.

Still further, since the method of measuring objects in the present invention uses the biosensor described above, it is possible to carry out the measurement rapidly, simply and accurately without washing-out the unbound labeled material.

The invention claimed is:

1. A method of assaying an object using a sensor comprising a magnetic sensor, which has a plurality of magnetic field detection elements arranged two dimensionally in X rows and Y columns, where X and Y are natural numbers, the plurality of the magnetic field detection elements each generating an output value according to an intensity of a detected magnetic field, the sensor measuring an amount of magnetic particles on the magnetic sensor based on the output values, the magnet particles being specifically bound to the object that is bound to the magnetic sensor, the magnet particles being bound to the magnetic sensor through the object, the method comprising:

applying a first magnetic field in which the magnet particles are between initial permeability and maximum permeability and a second magnetic field which is stronger than the first magnetic field and in which magnetization of a part or whole of the magnetic particles are saturated to the magnetic sensor bound to the magnetic particles through the object;

determining the amount of the magnetic particles of each of the plurality of the magnetic field detection elements, the amount of the magnetic particles being proportional to a difference between a first dispersion index of a first output value distribution of the first magnetic field and a second dispersion index of a second output value distribution of the second magnetic field obtained from an identical magnetic field detection element of the plurality of the magnetic field detection elements, the dispersion index being at least one of standard deviation, average deviation, and variance; and determining an amount of the object based on the amount of the magnetic particles determined.

2. The method according to claim 1, wherein coupling of the magnetic sensor and the object and coupling of the object and the magnetic particles are carried out at the same time in a reaction vessel including the magnetic sensor.

3. The method according to claim 1 or claim 2, wherein the applying firstly applies the first magnetic field to obtain the output values from the plurality of the magnetic field detection elements, and then applies the second magnetic field to obtain the output values from the plurality of the magnetic field detection elements.

4. The method according to claim 1 or claim 2, wherein the applying applies an external magnetic field vertically to the magnetic sensor.

5. The method according to claim 1 or claim 2, wherein other magnetic particles are associated with the magnetic particles bound to the magnetic sensor in a direction where a magnetic flux of the external magnetic field is formed.

6. The method according to claim 1 or claim 2, wherein the plurality of the magnetic field detection elements generate the output values in proportion to a magnetic flux density of a magnetic flux formed in a detection space where the magnetic field is detectable.

7. The method according to claim 1 or claim 2, wherein the plurality of the magnetic field detection elements each comprise a hall element.

* * * * *